US008454748B2

(12) United States Patent
Iwaki et al.

(10) Patent No.: US 8,454,748 B2
(45) Date of Patent: Jun. 4, 2013

(54) METHOD OF CALCULATING CARRIER MOBILITY

(75) Inventors: Yuji Iwaki, Atsugi (JP); Motoki Nakashima, Atsugi (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 1015 days.

(21) Appl. No.: 11/643,894

(22) Filed: Dec. 22, 2006

(65) Prior Publication Data

US 2007/0150206 A1 Jun. 28, 2007

(30) Foreign Application Priority Data

Dec. 27, 2005 (JP) ................................. 2005-376715

(51) Int. Cl.
*C30B 33/00* (2006.01)

(52) U.S. Cl.
USPC .................. 117/85; 117/201; 700/28; 700/91; 700/93

(58) Field of Classification Search
USPC ................................................... 117/85, 201
See application file for complete search history.

(56) References Cited

U.S. PATENT DOCUMENTS

| | | | | |
|---|---|---|---|---|
| 6,026,422 A * | 2/2000 | Yamada et al. | ................ | 708/523 |
| 6,237,529 B1 * | 5/2001 | Spahn | ........................... | 118/726 |
| 6,447,605 B1 * | 9/2002 | Chung et al. | .................... | 117/95 |
| 6,685,772 B2 * | 2/2004 | Goddard et al. | ................... | 117/3 |
| 7,074,270 B2 * | 7/2006 | Sato et al. | ........................... | 117/3 |
| 7,154,602 B2 * | 12/2006 | Wachsmuth | .................... | 356/417 |
| 7,343,277 B2 * | 3/2008 | Takada et al. | .................... | 703/21 |
| 2004/0257562 A1 * | 12/2004 | Wachsmuth | .................... | 356/317 |
| 2006/0211183 A1 * | 9/2006 | Duan et al. | ..................... | 438/149 |
| 2007/0150206 A1 * | 6/2007 | Iwaki et al. | ..................... | 702/19 |
| 2007/0176824 A1 * | 8/2007 | Stumbo et al. | ................ | 342/372 |

FOREIGN PATENT DOCUMENTS

| | | |
|---|---|---|
| JP | 05-267421 A | 10/1993 |
| JP | 09-063768 A | 3/1997 |

OTHER PUBLICATIONS

K. Bhattacharyya et al, Monte Carlo simulation of electron transport in alternating-current thin-film electroluminescent devices, J. Appt. Phys., vol. 73, No. 7, Apr. 1, 1993, pp. 3390-3395.*

(Continued)

*Primary Examiner* — Bob M Kunemund
(74) *Attorney, Agent, or Firm* — Eric J. Robinson; Robinson Intellectual Property Law Office, P.C.

(57) ABSTRACT

A calculation method for finding the hole mobility or the electron mobility of an organic film. The method includes the steps of: calculating the electron density of a film using semi-empirical quantum molecular dynamics calculations; using the fact that holes and electrons move easily through regions of high electron density to calculate the probability that a hole or an electron will move in an excited state in which an electron is excited from the HOMO (highest occupied molecular orbital) to the LUMO (lowest unoccupied molecular orbital) using a Monte Carlo method; and, using the probability as a performance index, calculating the hole mobility from the number of carriers which exist in the HOMO and the orbitals below the HOMO, or calculating the electron mobility from the number of carriers which exist in the LUMO and the orbitals above the LUMO.

17 Claims, 6 Drawing Sheets

OTHER PUBLICATIONS

M. Redecker et al, Determination of the Hole Mobility in Organic Light-Emitting Diodes via Transient Absorption, J. Phys. Chem. B, Jul. 13, 1997, 101, pp. 7398-7403.*

P. D'Angelo et al, Electrical transport properties characterization of PVK (poly N-vinyl carbazole) for electroluminescent devices applications, Elsevier-Solid-State Electronics 51 (2007), pp. 123-129.*

M. Brandbyge et al., *Density-Functional Method for Nonequilibrium Electron Transport*, Physical Review B, vol. 65, Mar. 22, 2002, pp. 165401-1-165401-17.

T. Masuda et al., *Tight-Binding Quantum Chemical Molecular Dynamics Simulation of Boron Activation Process in Crystalline Silicon*, Applied Surface Science, vol. 244, May 15, 2005, pp. 30-33.

* cited by examiner

METHOD OF CALCULATING CARRIER MOBILITY

BACKGROUND OF THE INVENTION

1. Field of the Invention

The present invention relates to a method of calculation which estimates carrier mobility. In particular, the invention relates to a method of calculation which estimates the hole mobility and the electron mobility of a molecular film used for an organic electroluminescent element.

2. Description of the Related Art

In the evaluation of an organic electroluminescent element, the carrier mobility of an organic material is an important parameter that influences the characteristics of the element. The carrier mobility of an organic material can be estimated by fitting using a model formula of mobility in the space charge limited current region of a current-voltage (I-V) curve of a film formed of the material A Time of Flight (TOF) method is commonly used to directly measure the carrier mobility of organic materials which have insulating properties, and a lot of research has been conducted on carrier transportability.

However, because a film thickness of about 1 to 2 μm is necessary for measurements using the TOF method, when forming a film by vacuum evaporation or the like, a lot of material must be expended. Further, since a transient photo-current curve cannot be seen clearly in measurements using the TOF method, it is also difficult to quantitatively estimate carrier mobility. In particular, it is difficult to quantitatively estimate the carrier mobility of a composite film formed from two or more materials.

Further, in the design of organic electroluminescent materials, besides estimates of electronic states such as the highest occupied molecular orbital (HOMO) level, the lowest unoccupied molecular orbital (LUMO) level, and the band gap by molecular orbital calculations, if estimates of hole mobility and electron mobility could be made, the design of materials that have charge transportability taken into consideration for each layer of an organic electroluminescent element would be possible.

Furthermore, for calculations concerning estimates of the electrical conduction properties of nanoscale devices, there is TranSIESTA-C. TranSIESTA-C is software which calculates voltage-current characteristics for two-probe systems under finite bias, based on density functional theory and non-equilibrium Green's function theory. In the two-probe systems, molecules are sandwiched between two electrodes. TranSIESTA-C can be applied to isolated molecular systems or to periodic systems such as crystals (for example, see Reference 1). However, this calculation software does not calculate the hole mobility or the electron mobility of an organic film, and from the standpoint of developing organic electroluminescent materials, the hole mobility and electron mobility of an organic film is important information.

[Reference 1] M. Brandbyge, J. L. Mozos, P. Ordejon, J. Taylor, K. Stokbro, Phys. Rev. B. 65, 165401 (2002)

SUMMARY OF THE INVENTION

In view of the foregoing, an object of the present invention is to provide a method which enables finding the hole mobility or the electron mobility of an organic film by calculation, from the standpoint of designing organic electroluminescent materials.

The present invention achieves the aforesaid object using a means described below.

In a method of calculation of carrier mobility relating to this invention, electron density is calculated using a semi-empirical quantum molecular dynamics calculation method, and using the fact that holes and electrons easily move through a region where the electron density is high, the probability that a hole or an electron will move is calculated using a Monte Carlo method, and then, using that probability as a performance index, the hole mobility or the electron mobility is found.

In a method of calculation of the carrier mobility of a film relating to this invention, the electron density of a film is calculated by a semi-empirical quantum molecular dynamics calculation method, and using the fact that holes and electrons easily move through a region where the electron density is high, the probability that a hole or an electron will move in an excited state in which an electron is excited from the highest occupied molecular orbital (also referred to as the highest occupied molecular orbit) to the lowest unoccupied molecular orbital (also referred to as the lowest unoccupied molecular orbit) is calculated using a Monte Carlo method, and then, using that probability as a performance index, the hole mobility is calculated from the number of carriers that exist in the highest occupied molecular orbital and the orbitals below it, or the electron mobility is calculated from the number of carriers that exist in the lowest unoccupied molecular orbital and the orbitals above it.

As the above film, a molecular film which forms any one of a charge injecting layer, a charge transport layer, and a light emitting layer of an organic electroluminescent element can be used.

An initial condition (an input parameter) of the semi-empirical quantum molecular dynamics calculation method is determined such that the highest occupied molecular orbital level, the lowest unoccupied molecular orbital level, and the band gap between the highest occupied molecular orbital and the lowest unoccupied molecular orbital of the aforesaid film, which are obtained with the semi-empirical quantum molecular dynamics calculation method, fall within an error range of $-0.2$ to $0.2$ eV inclusive, $-0.2$ to $0.2$ eV inclusive, and $-0.1$ to $0.1$ eV inclusive, respectively, with respect to measured values or values obtained by a first principles calculation method.

As the afore-mentioned first principles calculation method, a non-empirical molecular orbital method can be used. As a non-empirical molecular orbital method, the Hartree-Fock (HF) method, a second-order perturbation with electron correlation taken into account (a 2nd order Moller-Plesset perturbation: MP2) method, a fourth-order perturbation with electron correlation taken into account (a 4th order Moller-Plesset perturbation: MP4) method, or a method in which, taking electron correlation and an excited state into account, the interaction between electron configurations is found (a quadratic configuration interaction: QCISD) method is used. As a basis function, for inner-shell orbitals a contracted function employing six Gaussian functions is considered. For an orbital of the outermost shell three kinds of Slater-type orbitals are considered, and concerning these, for the Slater-type orbital which is close to the nucleus, three Gaussian functions are used, for the Slater-type orbital which is further from the nucleus, one Gaussian function is used, and for the Slater-type orbital which is between the Slater-type orbital which is close to the nucleus and the Slater-type orbital which is further from the nucleus, one Gaussian function or no Gaussian function is used. An initial condition of the semi-empirical quantum molecular dynamics calculation method is adjusted based on results calculated by the contracted function, which employs a contraction orbital exponent and a contraction coefficient.

As the above basis function, any one of 6-31 G (d), 6-31 G (d, p), 6-311 G (d, p) and LanL2DZ can be used.

Note that the QCISD method is a method in which the interaction between electron configurations is found, taking electron correlation and an excited state into account. The QCISD method takes into account up to and including a second order electron correlation which integrates interaction between configurations. Further, the MP2 method and the MP4 method are many-body interelectronic perturbation methods which take electron correlation into account. Furthermore, among the basis functions, 6-311 G, for example, is a basis function which considers a contracted function employing six Gaussian functions for an inner-shell orbital, and three kinds of Slater-type orbitals for an orbital of the outermost shell. For the Slater-type orbital which is close to the nucleus, three Gaussian functions are used, for the Slater-type orbital which is further from the nucleus, one Gaussian function is used, and for the Slater-type orbital which is between the Slater-type orbital which is close to the nucleus and the Slater-type orbital which is further from the nucleus, one Gaussian function is used. In 6-311 G anisotropy is given using a contracted function employing a contraction orbital exponent and a contraction coefficient, so as to raise the degree of approximation.

Further, as the first principles calculation method, a density functional method can be used. In that case, the density functional method is used as an electron correlation method, and as a basis function, for an inner-shell orbital a contracted function employing six Gaussian functions is considered, and for an orbital of the outermost shell three kinds of Slater-type orbitals are considered. Concerning the Slater-type orbitals considered for an orbital of the outermost shell, for the Slater-type orbital which is close to the nucleus, three Gaussian functions are used, for the Slater-type orbital which is further from the nucleus, one Gaussian function is used, and for the Slater-type orbital which is between the Slater-type orbital which is close to the nucleus and the Slater-type orbital which is further from the nucleus, one Gaussian function or no Gaussian function is used. An initial condition of the aforementioned semi-empirical quantum molecular dynamics calculation method is adjusted based on results calculated using the contracted function which employs a contraction orbital exponent and a contraction coefficient.

An initial condition of the semi-empirical quantum molecular dynamics calculation method is adjusted based on results calculated using any one of 6-31 G (d), 6-31 G (d, p), 6-311 G (d, p) and LanL2DZ as a basis function, and Becke's Three Parameter Hybrid Method Using the LYP Correlation (B3LYP) or Becke's Three Parameter Hybrid Method Using the PW91 Correlation (B3PW91) as a keyword for the above-mentioned density functional method.

In a method of calculation relating to the present invention that calculates the carrier mobility of a film whose carrier mobility is unknown, the electron density of a film whose carrier density is known and of the film whose carrier mobility is unknown are calculated using a semi-empirical quantum molecular dynamics calculation method, and using the fact that holes and electrons move easily through regions where electron density is high, the probability that a hole or an electron of the film whose carrier mobility is known and of the film whose carrier mobility is unknown will move in an excited state in which an electron is excited from a highest occupied molecular orbital to a lowest unoccupied molecular orbital is found by using a Monte Carlo method. Using these probabilities as performance indices, a parameter is computed using the ratio of the actual measured hole mobility or electron mobility of the film whose carrier mobility is known to the performance index of the film whose carrier mobility is known. Then, the hole mobility or the electron mobility of the film whose carrier mobility is unknown is obtained using that parameter and the performance index of the film whose carrier mobility is unknown.

As the film whose carrier mobility is known and the film whose carrier mobility is unknown, a molecular film which forms any one of a charge injecting layer, a charge transport layer, and a light emitting layer of an organic electroluminescent element can be used.

An initial condition (an input parameter) of the semi-empirical quantum molecular dynamics calculations method is determined such that the highest occupied molecular orbital level, the lowest unoccupied molecular orbital level, and the band gap between the highest occupied molecular orbital and the lowest unoccupied molecular orbital of the film whose carrier mobility is known and of the film whose carrier mobility is unknown, which are obtained by the semi-empirical quantum molecular dynamics calculation method, fall within an error range of −0.2 to 0.2 eV inclusive, −0.2 to 0.2 eV inclusive, and −0.1 to 0.1 eV inclusive, respectively, with respect to measured values or values obtained by a first principles calculation method.

As the first principles calculation method, a non-empirical molecular orbital method or a density functional method can be used.

As the non-empirical molecular orbital method, the Hartree-Fock (HF) method, a second-order perturbation (MP2) method with electron correlation taken into account, a fourth-order perturbation (MP4) method with electron correlation taken into account, or a method in which taking electron correlation and an excited state into account, the interaction between electron configurations is found (a QCISD method) is used. As a basis function, for an inner-shell orbital a contracted function employing six Gaussian functions is considered, and for an orbital of the outermost shell three kinds of Slater-type orbitals are considered. Concerning the Slater-type orbitals considered for an orbital of the outermost shell, for the Slater-type orbital which is close to the nucleus, three Gaussian functions are used, for the Slater-type orbital which is further from the nucleus, one Gaussian function is used, and for the Slater-type orbital which is between the Slater-type orbital which is close to the nucleus and the Slater-type orbital which is further from the nucleus, one Gaussian function or no Gaussian function is used. An initial condition of the semi-empirical quantum molecular dynamics calculation method is adjusted based on results calculated by the contracted function, which employs a contraction orbital exponent and a contraction coefficient.

Note that as the basis function, any one of 6-31 G (d), 6-31 G (d, p), 6-311 G (d, p), and LanL2DZ can be used.

Further, a density functional method can be used as the first principles calculation method. In that case, the density functional method is used as an electron correlation method, and as a basis function, for an inner-shell orbital a contracted function employing six Gaussian functions is considered, and for an orbital of the outermost shell three kinds of Slater-type orbitals are considered. Concerning the Slater-type orbitals considered for an orbital of the outermost shell, for the Slater-type orbital which is close to the nucleus, three Gaussian functions are used, for the Slater-type orbital which is further from the nucleus, one Gaussian function is used, and for the Slater-type orbital which is between the Slater-type orbital which is close to the nucleus and the Slater-type orbital which is further from the nucleus, one Gaussian function or no Gaussian function is used. An initial condition of the semi-empirical quantum molecular dynamics calculation method is adjusted based on results calculated using the contracted function, which employs a contraction orbital exponent and a contraction coefficient.

An initial condition of the semi-empirical quantum molecular dynamics calculation method is adjusted based on results calculated using any one of 6-31 G (d), 6-31 G (d,p), 6-311 G (d,p) and LanL2DZ as a basis function for the density functional method and using Becke's Three Parameter Hybrid Method Using the LYP Correlation (B3LYP) or Becke's Three Parameter Hybrid Method Using the PW91 Correlation (B3PW91) as a keyword of the electron correlation correction. Thus, the initial condition can be derived with good accuracy.

The material of the film is not limited to an organic electroluminescent (EL) material. Hole mobility or electron mobility can also be estimated for organic materials in general, organometallic complexes, inorganic materials, organic-inorganic compound materials, semiconductors, and insulators.

In comparison with TOF measurements, which require a large amount of material for the manufacture of a measurement sample and which cannot measure some materials, when a calculation method such as the above is used, the carrier mobility of any kind of organic or inorganic material thin film can be estimated. Information on carrier mobility is extremely important in regard to designing element structure and testing characteristics of organic electroluminescent elements. In particular, in the design of charge injection material, charge transport material, and host material and dopant material for a light emitting layer, hitherto, molecular properties such as the highest occupied molecular orbital level, the lowest unoccupied molecular orbital level, the band gap, the lowest triplet excitation level, and the glass transition temperature have been estimated using molecular orbital calculations and molecular dynamics calculations. However, using the calculation method of the present invention, it is possible to design novel materials taking carrier mobility into account quantitatively.

DETAILED DESCRIPTION OF THE INVENTION

The invention will be described below by way of an illustrative embodiment mode, with reference to the accompanying drawings. However, the invention can be carried out in many different modes, and those skilled in the art will appreciate that a variety of substitutions and modifications can be made to the embodiment mode without departing from the spirit and scope of the invention. Accordingly, the present invention is not to be construed as being limited to the embodiment mode described below.

[Embodiment Mode 1]

In this embodiment mode, for example, Colors-Excite, which is software for tight-binding quantum molecular dynamics calculations that is used on pages 30 to 33 of Applied Surface Science, 244 (2005), is used. Further, the hole mobility or electron mobility of models such as a bulk model or a surface model is calculated. When geometry optimization of these models is conducted using the tight-binding quantum molecular dynamics calculations software Colors-Excite, which is a semi-empirical quantum molecular dynamics calculation method, the ionization potential of an atom and the interaction between a pair of atoms are determined based on results of density functional theory (DFT) calculations, and are used as initial input parameters (initial conditions) of the tight-binding quantum molecular dynamics calculations. Whether the molecular orbital energy obtained is appropriate or not is determined by whether the highest occupied molecular orbital level and the band gap between the highest occupied molecular orbital and the lowest unoccupied molecular orbital are equal to or almost equal to measured values. Error ranges for the highest occupied molecular orbital level and the lowest unoccupied molecular orbital level are kept within −0.2 to 0.2 eV inclusive (preferably within −0.02 to 0.02 eV inclusive) and the error range for the band gap is kept within −0.1 to 0.1 eV inclusive (preferably within −0.01 to 0.01 eV inclusive). By setting the error ranges in this manner, an appropriate molecular orbital energy can be obtained.

In the case where the highest occupied molecular orbital level and the band gap between the highest occupied molecular orbital and the lowest unoccupied molecular orbital, which are calculated by the tight-binding quantum molecular dynamics calculations, do not fall within the error ranges, the input parameters used for the tight-binding quantum molecular dynamics calculations are modified such that they do fall within the error ranges. In a case where the goal is estimation of unknown characteristics of a material, in a one-molecule model, the highest occupied molecular orbital level is calculated by DFT calculations, and the excitation energy of an electron that reaches the lowest excited singlet state (S1) is calculated by TD-DFT (time-dependent density functional theory) calculations and defined as the band gap. Subsequently, the input parameters used for the tight-binding quantum molecular dynamics calculations are repeatedly modified such that the highest occupied molecular orbital level and the band gap between the highest occupied molecular orbital and the lowest unoccupied molecular orbital obtained by the tight-binding quantum molecular dynamics calculations match the highest occupied molecular orbital level and the S1 excitation energy of the one-molecule model obtained by DFT calculations, respectively.

Note that for the density functional calculations, as a basis function any one of 6-31 G (d), 6-31 G (d, p), 6-311 G (d, p), and LanL2DZ can be used, and as a keyword, B3LYP or B3PW91 can be used. These methods are limited to when measured values exist or to a model for which calculations can be performed by DFT. For models other than that, the initial input parameters of the tight-binding quantum molecular dynamics calculations are employed.

Further, instead of density functional theory (DFT) method calculations, a non-empirical molecular orbital calculation method can be used. In the case of using a non-empirical molecular orbital calculation method, the Hartree-Fock (HF) method, an MP2 method, an MP4 method, or a QCISD method can be employed. Further, based on results calculated using any one of 6-31 G (d), 6-31 G (d, p), 6-311 G (d, p) and LanL2DZ as a basis function, input parameters used for the tight binding quantum molecular dynamics calculations are repeatedly modified.

Next, the orbital energy of an excited state in which an electron is excited from the highest occupied molecular orbital to the lowest unoccupied molecular orbital is calculated for the above model, in which geometry optimization has been conducted by Colors-Excite. At that time, a state is considered in which a hole exists in the highest occupied molecular orbital and an electron exists in the lowest unoccupied molecular orbital. That is, for the highest occupied molecular orbital and the levels below the highest occupied molecular orbital, hole mobility is considered, and for the lowest unoccupied molecular orbital and the levels above the lowest unoccupied molecular orbital, electron mobility is considered.

Next, in an excitation state in which one electron is excited from the highest occupied molecular orbital to the lowest unoccupied molecular orbital, the ease of movement of a carrier is evaluated by a Monte Carlo method. At that time, evaluation sections are designated by dividing a cell containing a molecular model into a suitable number of regions. Because holes or electrons move through regions where electron density is high, the probability that a carrier will move is calculated by a Monte Carlo method for each orbital. The probability that a carrier will move refers to the number of times a carrier moves with respect to the number of trials, and this is considered to be performance index A. Further, the number of carriers N is regarded as conforming to the Fermi distribution, and the number of carriers in each orbital, H, is calculated. The product of the performance index A and the number of carriers H is the performance index of electrical conductivity $\sigma^*$.

Further, electrical conductivity is expressed by Formula (1) below.

[Formula 1]

$$\sigma = NQ\mu = q(p\mu_p + n\mu_n) \tag{1}$$

Here, $\sigma$ is the electrical conductivity, N is the number of carriers, $\mu$ is the mobility, and Q and q are the elementary charge ($1.602 \times 10^{-19}$ C). p and n show the hole concentration and the electron concentration, respectively. Further, according to Formula (1), electrical conductivity can be expressed by the sum of the terms relating to the hole mobility $\mu_p$ and the electron mobility $\mu_n$. Therefore, in the case where $\sigma$ for the highest occupied molecular orbital and the levels below it is defined as electrical conductivity $\sigma_p$ which only takes hole movement into account, and $\sigma$ for the lowest unoccupied molecular orbital and the levels above it is defined as electrical conductivity $\sigma_n$ which only takes electron movement into account, $\sigma_p$ and $\sigma_n$ can be expressed by Formula (2) and Formula (3), shown below.

[Formula 2]

$$\sigma_p = qp\mu_p \tag{2}$$

[Formula 3]

$$\sigma_n = qn\mu_n \tag{3}$$

In the case of calculating the hole mobility $\mu_p$, if the hole mobility per unit volume performance index $\sigma_p{}'$ is used with respect to the electrical conductivity $\sigma_p$ calculated by a Monte Carlo method, Formula (2) and Formula (3) become Formula (4) and Formula (5), shown below.

[Formula 4]

$$\sigma_p{}' = qp\mu_p{}' \tag{4}$$

[Formula 5]

$$\sigma_n{}' = qn\mu_n{}' \tag{3}$$

Treating hole concentration p ($cm^{-3}$) as the reciprocal of cell volume, the hole mobility per unit volume $\mu_p{}'$ can be estimated using Formula (4). In the case of calculating the electron mobility per unit volume $\mu_n{}'$, it can be estimated similarly using Formula (5). The performance index for hole mobility per unit volume is used because depending on the model, cell size and the evaluation sections calculated by a Monte Carlo method may differ. Further, here, $\sigma_p{}'$ is merely an indicator, so it is necessary to convert $\sigma_p{}'$ to a value which matches the mobility data of measured values. Therefore, known data of a material, for example, hole mobility data, obtained by TOF measurements or the like, and the hole mobility per unit volume performance index $\sigma_p{}'$ of these calculations, are used for the conversion. Therefore, introducing the reduced value, Parameter a, Formula (4) can be rewritten as in Formula (6) below.

[Formula 6]

$$a\sigma_p{}' = qp\mu(p) \tag{6}$$

Here, $\mu(p)$ is the hole mobility which is being sought. Similarly, for electron mobility, Formula (5) can be rewritten as in Formula (7) below by introducing Parameter b.

[Formula 7]

$$b\sigma_n{}' = qn\mu(n) \tag{7}$$

Here, $\mu(n)$ is the electron mobility which is being sought.

In the above manner, hole mobility and the electron mobility can be found by simulation. Therefore, it is possible to find the carrier mobility of films formed from organic material and of films formed from inorganic material and the like, which until now could not be measured.

In the case of an organic electroluminescent element, the calculation method of the present invention can be applied to materials that are used for layers including a light emitting material that are interposed between an anode and a cathode, that is, layers which have a function such as hole transport, hole injection, electron transporting, electron injection, or light emitting, and the carrier mobility of each material can be estimated.

A hole injection layer is a layer provided between an anode and a hole transport layer. As a hole injection layer, a mixed layer of an organic compound and a metal oxide can be used.

As a metal oxide, for example, zirconium oxide, hafnium oxide, vanadium oxide, niobium oxide, tantalum oxide, chromium oxide, molybdenum oxide, tungsten oxide, titanium oxide, manganese oxide, or rhenium oxide can be used.

As an organic compound, for example, an organic material having an arylamino group can be used, such as 4,4'-bis[N-(1-naphthyl)-N-phenylamino]biphenyl (abbrev.: NPB), 4,4'-bis[N-(3-methylphenyl)-N-phenylamino]biphenyl (abbrev.: TPD), 4,4',4''-tris(N,N-diphenylamino)triphenylamine (abbrev.: TDATA), 4,4',4''-tris[N-(3-methylphenyl)-N-phenylamino]triphenylamine (abbrev.: MTDATA), 4,4'-bis{N-[4-(N,N-di-m-tolylamino)phenyl]-N-phenylamino}biphenyl (abbrev.: DNTPD), 1,3,5-tris[N,N-di(m-tolyl)amino]benzene (abbrev.: m-MTDAB), or 4,4',4''-tris(N-carbazolyl)triphenylamine (abbrev.: TCTA). Further, phthalocyanine (abbrev.: $H_2Pc$), copper phthalocyanine (abbrev.: CuPc), vanadyl phthalocyanine (abbrev.: VOPc), or the like can be used.

A hole transport layer is a layer provided between an anode and a light emitting layer. Further, in the case where a hole injection layer is provided, the hole transport layer is provided between the hole injection layer and the light emitting layer.

As the hole transport layer, for example, a layer formed from an aromatic amine compound (that is, a compound having a benzene ring-nitrogen bond) such as NPB, TPD, TDATA, MTDATA, BSPB (N,N'-diphenyl-N,N'-bis(spiro-9,9'-bifluorene-2-yl)benzidine) can be used.

A light emitting layer is a layer provided between an anode and a cathode. Further, in the case where a hole transport layer and an electron transport layer are provided, the light emitting layer is provided between the hole transport layer and the electron transport layer. There are two main forms of layers which serve as a light emitting layer. One is a host-guest type layer in which a light emitting material is dispersed through a layer formed from a material (a host material) which has a larger energy gap than that of the light emitting material (the dopant material) which serves as a light emitting center. The other is a light emitting layer formed only from a light emitting material. Examples that can be given of a light emitting material which serves as a light emitting center include 4-dicyanomethylene-2-methyl-6-[2-(1,1,7,7-tetramethyljulolidine-9-yl)ethenyl]-4H-pyran (abbrev.: DCJT), 4-dicyanomethylene-2-tert-butyl-6-( 1,1,7,7-tetramethyljulolidyl-9-yl) ethenyl)-4H-pyran, periflanthene, 2,5-dicyano-1,4-bis[2-(10-methoxy-1,1,7,7-tetramethyljulolidine-9-yl) ethenyl) benzene, N,N'-dimethylquinacridone (abbrev.: DMQd), coumarin 6, coumarin 545T, tris(8-quinolinolato)aluminum (abbrev.: $Alq_3$), 9,9'-bianthryl, 9,10-diphenylanthracene (abbrev.: DPA), and 9,10-di(2-naphthyl)anthracene (abbrev.: DNA), 2,5,8,11-tetra-(tert-butyl)perylene (abbrev.: TBP), PtOEP, $Ir(ppy)_3$, $Btp_2Ir(acac)$, FIrpic, and the like. Further, in a case where the layer in which a light emitting material is dispersed is formed, as a host material which serves as a host, an anthracene derivative such as 9,10-di(2-naphthyl)-2-tert-butylanthracene (abbrev.: t-BuDNA), a carbazole derivative such as 4,4'-di(N-carbazolyl)biphenyl (abbrev.: CBP), or a metal complex such as tris(8-quinolinolato)aluminum (abbrev.: $Alq_3$), tris(4-methyl-8-quinolinolato)aluminum (abbrev.: $Almq_3$), bis(10-hydroxybenzo[h]quinolinato)beryllium (abbrev.: $BeBq_2$), bis(2-methyl-8-quinolinolato)-4-phenylphenolato-aluminum (abbrev.: BAlq), bis[2-(2'-hydroxyphenyl)pyridinato]zinc (abbrev.: $Znpp_2$), or bis[2-(2'-hydroxyphenyl)benzoxazolato]zinc (abbrev.: $Zn(BOX)_2$) can be used, for example. Further, as a material which can be a light emitting material which solely forms a light emitting layer, tris(8-quinolinolato)aluminum (abbrev.: $Alq_3$), 9,10-di (2-naphthyl)anthracene (abbrev.: DNA), bis(2-methyl-8-quinolinolato)-4-phenylphenolato-aluminum (abbrev.: BAlq), or the like may be used.

The electron transport layer is a layer provided between a light emitting layer and a cathode. In the case where an electron injecting layer is provided, the electron transport layer is provided between the light emitting layer and the electron injecting layer. As the electron transport layer, for example, a layer formed from a metal complex having a quinoline skeleton or a benzoquinoline skeleton, such as tris (8-quinolinolato)aluminum (abbrev.: $Alq_3$), tris(4-methyl-8-quinolinolato)aluminum (abbrev.: $Almq_3$), bis(10-hydroxybenzo[h]quinolinato)beryllium (abbrev.: $BeBq_2$), or bis(2-methyl-8-quinolinolato)-4-phenylphenolato-aluminum (abbrev.: BAlq), or the like can be used. Alternatively, a metal complex having an oxazole-based or thiazole-based ligand, such as bis[2-(2'-hydroxyphenyl)benzoxazolato]zinc (abbrev.: $Zn(BOX)_2$), bis[2-(2'-hydroxyphenyl)benzothiazolato]zinc (abbrev.: $Zn(BTZ)_2$), or the like, can be used. In addition, other than a metal complex, 2-(4-biphenylyl)-5-(4-tert-butylphenyl)-1,3,4-oxadiazole (abbrev.: PBD), or 1,3-bis [5-(4-tert-butylphenyl)-1,3,4- oxadiazole-2-yl]benzene (abbrev.: OXD-7), 3-(4-biphenylyl)-4-phenyl-5-(4-tert-butylphenyl)-1,2,4-triazole (abbrev.: TAZ), 3-(4-biphenylyl) (-4-(4-ethylphenyl)-5-(4-tert-butylphenyl)- 1,2,4-triazole (abbrev.: p-EtTAZ), bathophenanthroline (abbrev.: BPhen), bathocuproine (abbrev.: BCP), or the like can be used.

An electron injecting layer is a layer provided between a cathode and an electron transport layer. As an electron injecting layer, for example, an alkali metal compound or an alkaline earth metal compound such as lithium fluoride (LiF), cesium fluoride (CsF), or calcium fluoride ($CaF_2$) can be used. Alternatively, a layer in which an alkali metal or an alkaline earth metal compound is included in a material having an electron transport property can be used. For example, a layer in which magnesium (Mg) is included in $Alq_3$, or the like can be used.

In the case of an inorganic electroluminescent element, a layer including a light emitting material in which luminescent particles are dispersed as a dispersing agent can be used.

For the luminescent particles, for example, ZnS with Cu (copper) doped with a donor impurity such as Cl (chlorine), I (iodine), or Al can be used.

As the dispersing agent, for example, a polymer with a relatively high dielectric constant, such as a cyanoethyl cellulose-based resin, or a resin such as polyethylene, polypropylene, a polystyrene-based resin, a silicone resin, an epoxy resin, or vinylidene fluoride can be used. Alternatively, high-dielectric constant-fine particles of, for example, $BaTiO_3$ (barium titanate), or $SrTiO_3$ (strontium titanate) can be moderately mixed with one of the above resins to adjust the dielectric constant, and this mixture can be used as a dispersing agent.

A dielectric layer may be interposed between the layer including a light emitting material and an electrode. As the dielectric layer, a material chosen from among metal oxides and nitrides, for example, $TiO_2$, $BaTiO_3$, $SrTiO_3$, $PbTiO_3$, $KNbO_3$, $PbNbO_3$, $Ta_2O_3$, $BaTa_2O_6$, $LiTaO_3$, $Y_2O_3$, $Al_2O_3$, $ZrO_2$, AlON, or ZnS is used.

The calculation method of the present invention may be applied to the materials described above, and the carrier mobility of each material can be estimated. Of course, the present invention is not limited to the materials enumerated here, and it is also possible to design a novel material taking carrier mobility into consideration quantitatively. Accordingly, low voltage drive and low current drive can be realized in a light emitting element including a charge transport layer, a charge injecting layer, and a light emitting layer, which is manufactured applying the calculation method of the present invention.

Embodiment 1

In this embodiment, an example in which the calculation method of the present invention is applied is explained. In the example, an organic electroluminescent material, 4,4'-bis[N-(1-naphthyl)-N-phenylamino]biphenyl (hereafter referred to as NPB) or 4,4'-bis(N-{4-[N,N-bis(3-methylphenyl)amino phenyl}-N-phenylamino)biphenyl (hereafter referred to as DNTPD), of which the carrier mobility was known, was used to find the hole mobility and the electron mobility of a composite film of NPB and molybdenum oxide or of a composite film of DNTPD and molybdenum oxide, of which the carrier mobility was unknown. Of course, the calculation method of the present invention is not limited to the materials mentioned in this embodiment, and can also be applied to other organic electroluminescent materials. In addition, the calculation method of the present invention can be applied to materials such as metal, inorganic semiconductors, organic semiconductors, insulating materials, and the like.

The current-voltage characteristics of an organic-inorganic composite film formed by co-vapor deposition of molybdenum oxide and NPB, which is a hole transport material, are superior to those of a film formed of NPB. Comparing the current-voltage curves of the two, the charge injection of a composite film of NPB and molybdenum oxide is far superior to that of a film formed of NPB. In order to make the reason for this clear, the carrier mobilities were calculated.

Below, an example is explained in which the hole mobility of a composite film of NPB and molybdenum oxide and of a composite film of DNTPD and molybdenum oxide were calculated using Colors-Excite, a tight-binding quantum molecular dynamics calculation software, and a Monte Carlo method.

Figure 1:
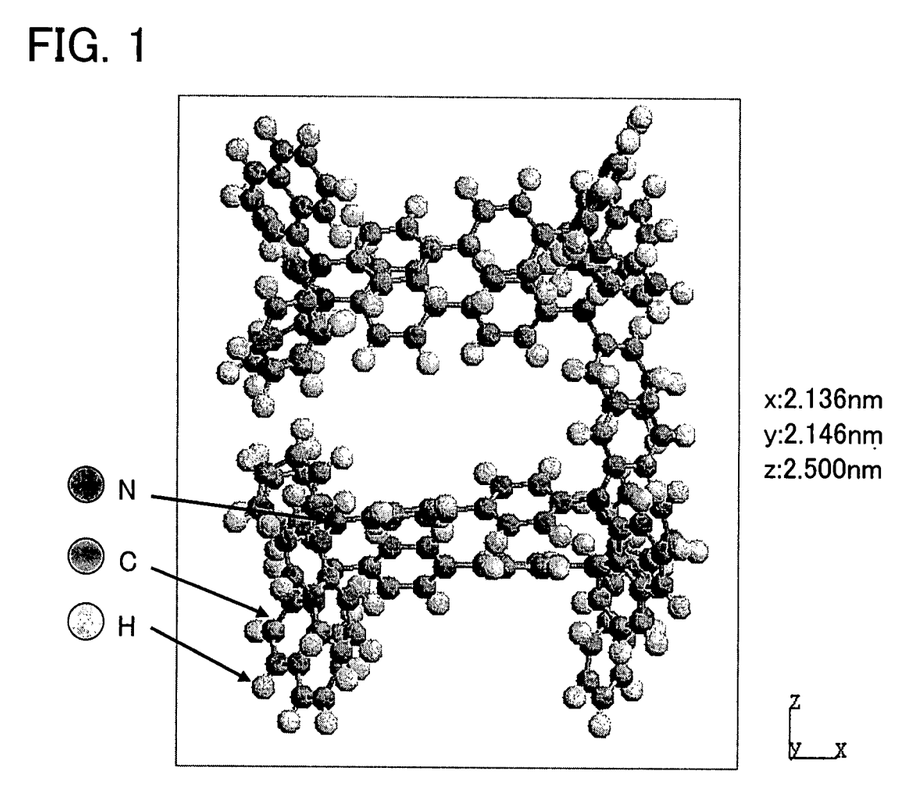
FIG. 1 is a model diagram of two NPB molecules inserted into a 2.136 nm×2.146 nm×2.500 nm cell and relaxed by molecular dynamics calculations.
Figure 2:
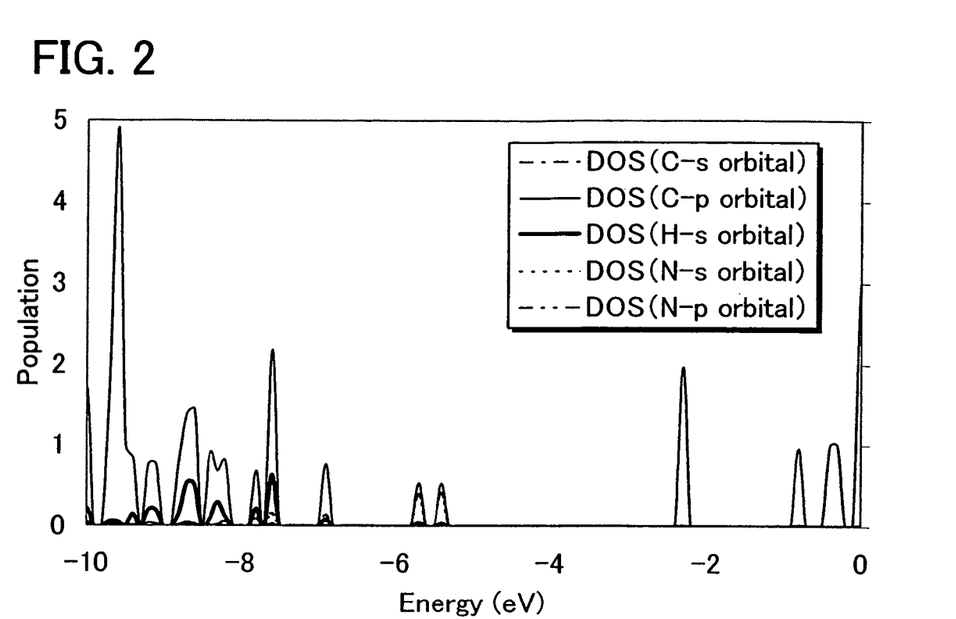
FIG. 2 shows density of states (DOS) for the NPB two-molecule model according to tight-binding quantum molecular dynamics calculations.

First, the highest occupied molecular orbital and the lowest unoccupied molecular orbital of NPB were calculated using the Colors-Excite software. FIG. 1 is a model of two molecules of NPB inserted into a 2.136 nm×2.146 nm×2.500 nm cell and relaxed by molecular dynamics calculations. In the model, the major axis directions of the NPB are oriented parallel to each other. FIG. 2 is a density of states graph of the model in FIG. 1. FIG. 2 shows the density of states (DOS) for s orbitals and p orbitals of C atoms, s orbitals and p orbitals of N atoms, and s orbitals of H atoms. Values obtained for the highest occupied molecular orbital level and the lowest unoccupied molecular orbital level according to density functional calculations were −5.36 eV and −2.33 eV, respectively.

Next, since the highest occupied molecular orbital level of NPB was able to be estimated by ambient photoelectron spectroscopy (using a Riken Keiki Co., Ltd. AC-2 spectroscope), and the band gap was able to be estimated from the UV-vis spectrum absorption edge, these measurement data were used as information for deciding whether the results of the density functional calculations were valid or not. The measured values of the highest occupied molecular orbital level and the lowest unoccupied molecular orbital level were −5.38 eV and −2.32 eV, respectively. The calculated values are within ±0.2 eV of the measured values, showing extremely good agreement.

Figure 3:
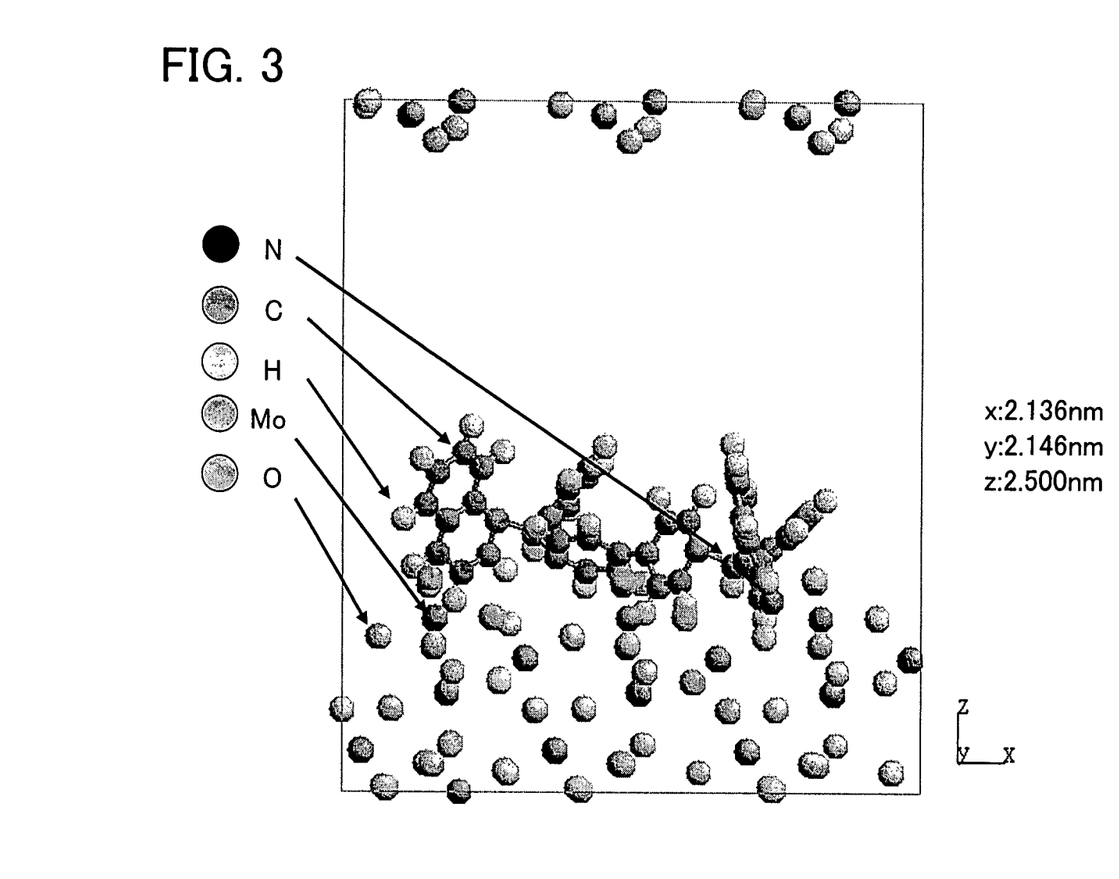
FIG. 3 is a model diagram of an NPB and molybdenum oxide composite material inserted into a 2.136 nm×2.146 nm×2.500 nm cell and relaxed by molecular dynamics calculations.
Figure 4:
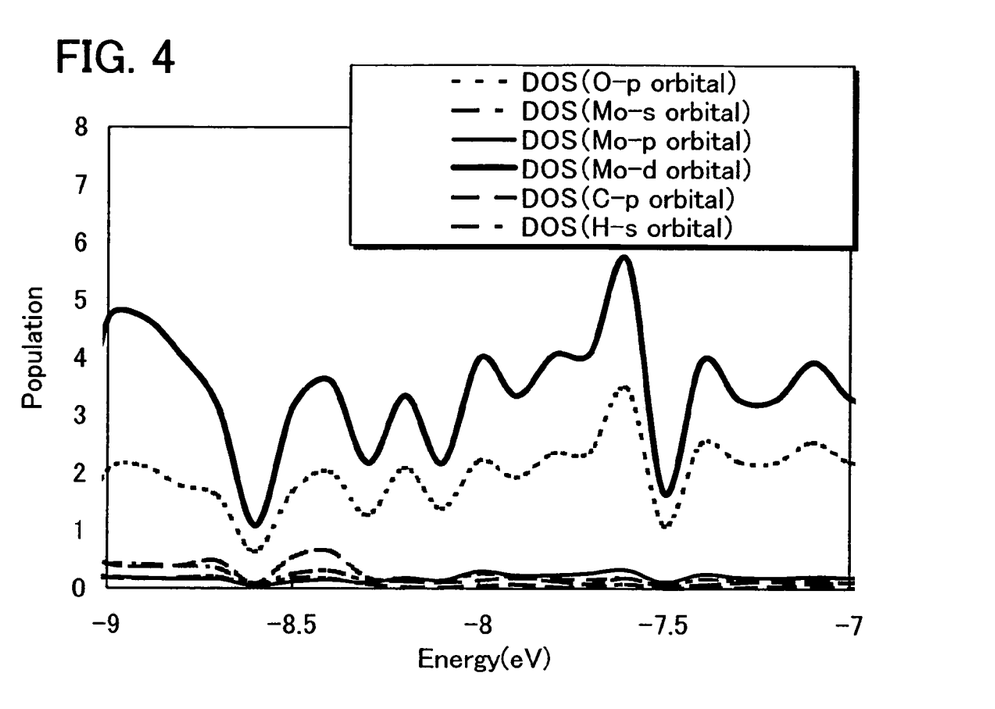
FIG. 4 shows density of states (DOS) for the NPB and molybdenum oxide composite material according to tight-binding quantum molecular dynamics calculations.
Figure 5:
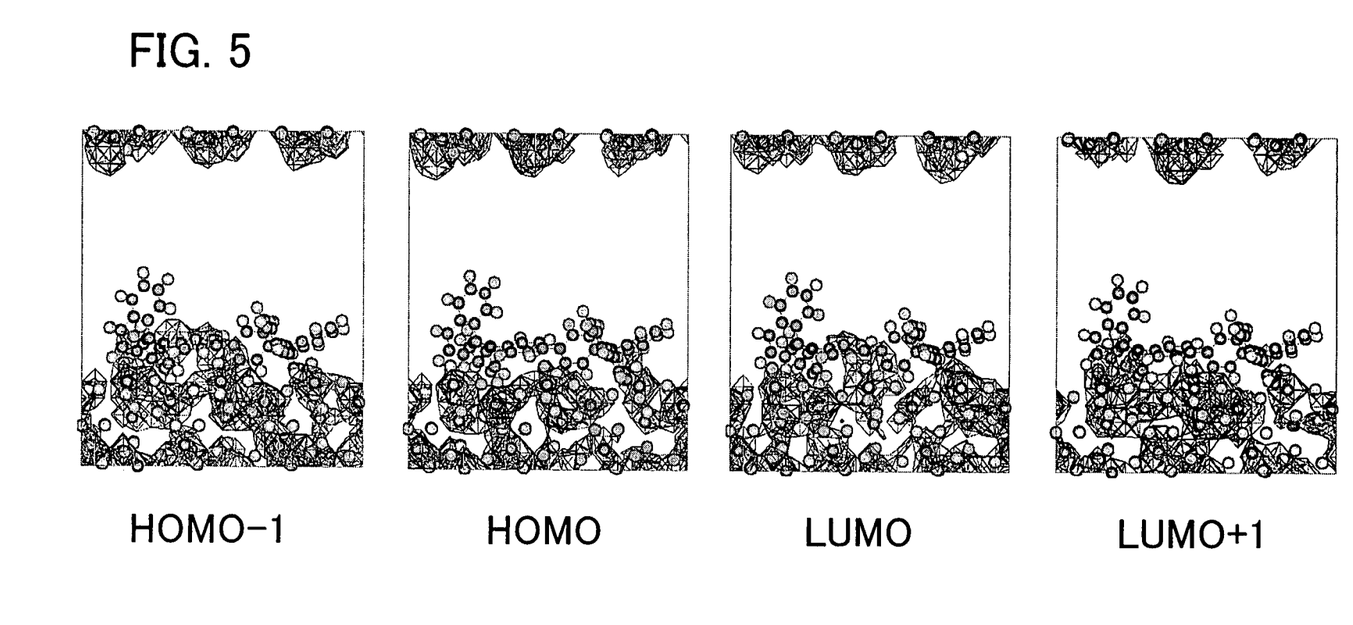
FIG. 5 shows molecular orbitals of the NPB and molybdenum oxide composite material.

FIG. 3 shows a model of a composite film of NPB and molybdenum oxide. The composite film model of FIG. 3 is an interface model relaxed by molecular dynamics calculations in which NPB and molybdenum oxide were placed in a 2.136 nm×2.146 nm×2.500 nm cell and NPB was adsorbed on the $MoO_3$ (100) face. FIG. 4 shows the density of states (DOS) in this model for the p orbitals of O atoms, the s orbitals, p orbitals and d orbitals of Mo atoms, the p orbitals of C atoms, and the s orbitals of H atoms. According to calculations using Colors-Excite (tight-binding quantum molecular dynamics calculations software), it was found that the band gap between the highest occupied molecular orbital and the lowest unoccupied molecular orbital was extremely small compared to that of NPB. Further, some of the molecular orbitals obtained from these calculations are shown in FIG. 5. In FIG. 5, four orbitals are shown—an orbital one level below the highest occupied molecular orbital level (hereafter referred to as HOMO−1), the highest occupied molecular orbital (HOMO), the lowest unoccupied molecular orbital (LUMO), and an orbital one level above the lowest unoccupied molecular orbital (hereafter referred to as LUMO+1). The straight lines in the figure indicate sections where regions of high electron density overlap.

The probability that a carrier would move in an excited state of the interface model of the NPB and molybdenum oxide composite film shown in FIG. 3 in which one electron was excited from the highest occupied molecular orbital to the lowest unoccupied molecular orbital was calculated by a Monte Carlo method. Holes move through regions having higher electron density. The relationship between regions where the electron density of NPB was high was considered, unit volume was set at 0.05 nm×0.05 nm×0.025 nm, and this was regarded as one mesh. In addition, a starting point and an end point were determined for an evaluation section, and ease of carrier movement between those points was evaluated. The number of movements per one million trials was regarded as the carrier mobility performance index A, and was calculated for each orbital. In addition, the number of carriers N was regarded as conforming to the Fermi distribution, and the number of carriers in each orbital, H, was calculated. The results of these calculations are shown in Table 1.

TABLE 1

| molecular orbital | 863 | 864 | 865 | 866 | 867 | 868 |
|---|---|---|---|---|---|---|
| orbital energy level (eV) | −8.434 | −8.423 | −8.389 | −8.38 | −8.373 | −8.345 |
| number of electrons | 2 | 2 | 1 | 1 | 0 | 0 |
| mobility performance index: A | 152.6667 | 113.6667 | 13.7778 | 2.2222 | 92.4444 | 50.6667 |
| orbital energy level (eV): B | −8.434 | −8.423 | −8.389 | −8.38 | −8.373 | −8.345 |
| standard energy level (eV): C | −8.389 | −8.389 | −8.389 | −8.389 | −8.389 | −8.389 |

TABLE 1-continued

| | | | | | | |
|---|---|---|---|---|---|---|
| Fermi level (eV): D = (B + C)/2 | −8.412 | −8.406 | −8.389 | −8.385 | −8.381 | −8.367 |
| energy gap (eV): E = B − D | 0.022 | 0.017 | 0.000 | 0.004 | 0.008 | 0.022 |
| value of Fermi distribution function: F | 2.95E−01 | 3.41E−01 | 5.00E−01 | 4.57E−01 | 4.23E−01 | 2.99E−01 |
| maximum number of carriers of orbital: G | 2 | 2 | 2 | 2 | 2 | 2 |
| number of carriers: H = F * G | 5.90E−01 | 6.82E−01 | 1.00E+00 | 9.13E−01 | 8.46E−01 | 5.98E−01 |
| performance index of electrical conductivity σ* = A * H | 90.1 | 77.6 | 13.8 | 2.0 | 78.2 | 30.3 |
| carrier | | hole | | | electron | |
| number of carriers per 1 cm³ (/cm³) | | 8.80E+19 | | | 9.11E+19 | |
| mobility (cm²/Vs) | | 5.10E−04 | | | 3.11E−04 | |

Table 1 shows molecular orbital numbers, orbital energy levels, the number of occupying electrons, and the mobility performance index A for an excited state of the interface model of the composite of NPB and molybdenum oxide in which one electron is excited from the highest occupied molecular orbital to the lowest unoccupied molecular orbital. The molecular orbitals were calculated at a temperature of 300 K, and carrier mobility was estimated for orbitals at an energy level in a range from the energy level of the highest occupied molecular orbital to 0.3 eV below the energy level of the highest molecular orbital and for orbitals at an energy level in a range from the energy level of the lowest unoccupied molecular orbital to 0.3 eV above the energy level of the lowest unoccupied molecular orbital. Table 1 concerns orbitals having a molecular orbital number in a range from two less than that of the highest occupied molecular orbital to two more than that of the lowest unoccupied molecular orbital. The highest occupied molecular orbital level was assumed to be at the standard energy level C. The Fermi level D was assumed to be midway between the energy level of an orbital B and the standard energy level C, and was calculated for each orbital. The difference between the energy level of an orbital B and the Fermi level D was regarded as the energy gap E, and was calculated for each orbital. From these values, the Fermi distribution value F was calculated. The number of carriers in each orbital, H, was able to be calculated from the Fermi distribution with respect to the maximum number of carriers, G, of the orbital. To obtain the performance index of electrical conductivity σ*, the mobility performance index A was multiplied by the number of carriers in an orbital, H. The performance index of electrical conductivity σ* was calculated for each orbital.

Concerning the highest occupied molecular orbital and the orbitals below it, the sum of the electrical conductivity performance indices σ* was regarded as the electrical conductivity with only hole mobility taken into account $\sigma_p$, and a value of $3.065 \times 10^2$ was obtained.

Next, the electrical conductivity with only hole mobility taken into account $\sigma_p$ of the above-mentioned interface model of the composite of NPB and molybdenum oxide was converted to a hole mobility per unit volume performance index $\sigma_p'$, and using Formula (6), the hole mobility, $\mu(p)=5.14\times10^{-4}$ (cm²/Vs), was calculated. Here, the reciprocal of cell volume, $8.73\times10^{19}$ (cm⁻³), was used as the hole concentration p (cm⁻³), and $1.602\times10^{-19}$ (C) was used as elementary charge q. For Parameter a, the ratio of the per unit volume $\mu_p'$ of NPB, which was obtained by similar calculations, and the measured μ(p) of NPB was used. The measured μ(p) of NPB was considered to be $1.00\times10^{-4}$ (cm²/Vs). The results of electrical conductivity calculations for NPB are shown in Table 2.

TABLE 2

| | | | | |
|---|---|---|---|---|
| molecular orbital | 108 | 109 | 110 | 111 |
| orbital energy level (eV) | −5.696 | −5.436 | −2.314 | −2.298 |
| number of electrons | 2 | 1 | 1 | 0 |
| mobility performance index: A | 84.1111 | 86.8889 | 135.6667 | 108.3333 |
| orbital energy level (eV): B | −5.696 | −5.436 | −2.314 | −2.298 |
| standard energy level (eV): C | −5.436 | −5.436 | −5.436 | −5.436 |
| Fermi level (eV): D = (B + C)/2 | −5.566 | −5.436 | −3.875 | −3.867 |
| energy gap (eV): E = B − D | 0.130 | 0.000 | 1.561 | 1.569 |
| value of Fermi distribution function: F | 6.5E−03 | 5.0E−01 | 5.8E−27 | 4.3E−27 |
| maximum number of carriers of orbital: G | 2 | 2 | 2 | 2 |
| number of carriers of each orbital: H = F * G | 1.3E−02 | 1.0E+00 | 1.2E−26 | 8.5E−27 |
| carrier | hole | | electron | |
| performance index of electrical conductivity σ' = A * H | 1.1 | 86.9 | 1.58E−24 | 9.23E−25 |

Table 2 shows the molecular orbital number, the orbital energy level, the number of occupying electrons, and the mobility performance index A for an excited state of NPB in which one electron is excited from the highest occupied molecular orbital to the lowest unoccupied molecular orbital. These were obtained similarly to those for the interface model of the composite of NPB and molybdenum oxide.

Further, the ground state (unexcited state) of the interface model of NPB and molybdenum oxide and the ground state (unexcited state) of NPB were calculated similarly, and the results are shown in Table 3 and Table 4, respectively.

TABLE 3

| molecular orbital | 863 | 864 | 865 | 866 | 867 | 868 |
|---|---|---|---|---|---|---|
| orbital energy level (eV) | −8.434 | −8.423 | −8.389 | −8.38 | −8.373 | −8.345 |
| number of electrons | 2 | 2 | 2 | 0 | 0 | 0 |
| mobility performance index: A | 152.6667 | 113.6667 | 13.7778 | 2.2222 | 92.4444 | 50.6667 |
| orbital energy level (eV): B | −8.434 | −8.423 | −8.389 | −8.38 | −8.373 | −8.345 |
| standard energy level (eV): C | −8.38 | −8.38 | −8.38 | −8.389 | −8.389 | −8.389 |
| Fermi level (eV): D = (B + C)/2 | −8.407 | −8.402 | −8.385 | −8.385 | −8.381 | −8.367 |
| energy gap (eV): E = B − D | 0.027 | 0.021 | 0.005 | 0.004 | 0.008 | 0.022 |
| value of Fermi distribution function: F | 2.60E−01 | 3.03E−01 | 4.57E−01 | 4.57E−01 | 4.23E−01 | 2.99E−01 |
| maximum number of carriers of orbital: G | 2 | 2 | 2 | 2 | 2 | 2 |
| number of carriers: H = F * G | 5.20E−01 | 6.06E−01 | 9.13E−01 | 9.13E−01 | 8.46E−01 | 5.98E−01 |
| performance index of electric conductivity $\sigma^* = A * H$ | 79.4 | 68.9 | 12.6 | 2.0 | 78.2 | 30.3 |
| carrier | | hole | | | electron | |
| number of carriers per 1 cm$^3$ (/cm$^3$) | | 7.78E+19 | | | 9.11E+19 | |
| mobility (cm$^2$/Vs) | | 4.52E−04 | | | 3.11E−04 | |

TABLE 4

| molecular orbital | 108 | 109 | 110 | 111 |
|---|---|---|---|---|
| orbital energy level (eV) | −5.696 | −5.436 | −2.314 | −2.298 |
| number of electrons | 2 | 2 | 0 | 0 |
| mobility performance index: A | 84.1111 | 86.8889 | 135.6667 | 108.3333 |
| orbital energy level (eV): B | −5.696 | −5.436 | −2.314 | −2.298 |
| standard energy level (eV): C | −2.314 | −2.314 | −5.436 | −5.436 |
| Fermi level (eV): D = (B + C)/2 | −4.005 | −3.875 | −3.875 | −3.867 |
| energy gap (eV): E = B − D | 1.691 | 1.561 | 1.561 | 1.569 |
| value of Fermi distribution function: F | 3.9E−09 | 4.3E−04 | 5.8E−27 | 4.3E−27 |
| maximum number of carriers of orbital: G | 2 | 2 | 2 | 2 |
| number of carriers of each orbital: H = F * G | 7.9E−09 | 8.7E−04 | 1.2E−26 | 8.5E−27 |
| Carrier | | hole | | electron |
| cell size (cm$^3$) | | 2.50E−12 | | |
| number of carriers (per cell) | | 8.7E−04 | | 2.0E−26 |
| number of carriers per 1 cm$^3$ (/cm$^3$) | | 3.48E+08 | | 8.1E−15 |

Figure 6:
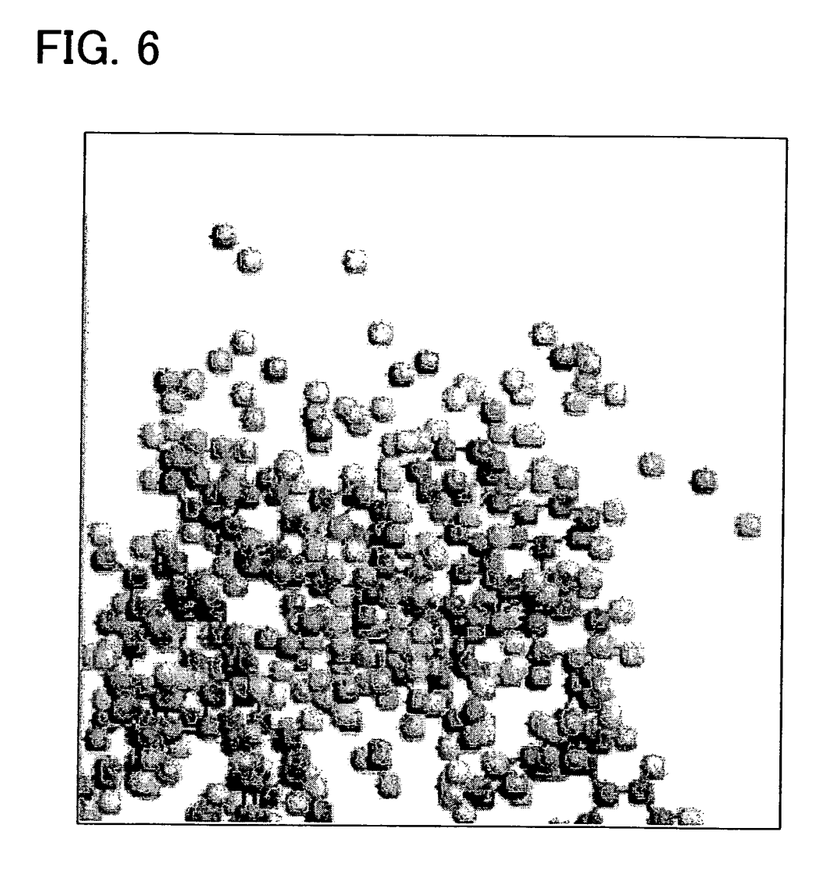
FIG. 6 is a model diagram of the NPB and molybdenum oxide composite material inserted into a 2.136 nm×2.146 nm×2.500 nm cell and relaxed by molecular dynamics calculations.

Further, similarly, calculations were conducted for a composite model in which 3 molecules of NPB and 2 clusters of Mo$_5$O$_{15}$ were inserted into one cell. FIG. 6 shows this composite model relaxed by molecular dynamics calculations.

The density of states (DOS) of the composite model shown in FIG. 6 was obtained by tight-binding quantum molecular dynamics calculations. In a similar manner as for the interface model, as orbitals in which an electron might make a transition at 300 K, orbitals whose energy level was in a range from the energy level of the highest occupied molecular orbital to −0.2 eV from the energy level of the highest occupied molecular orbital and orbitals whose energy level was in a range from the energy level of the lowest unoccupied molecular orbital to +0.2 eV from the energy level of the lowest unoccupied molecular orbital were selected. Further, a cell whose size was 2.136 nm×2.146 nm×2.500 nm was divided into the same number of evaluation sections as the above-mentioned interface model. The evaluation regions and the starting point and end point of hole movement or electron movement were specified by atomic coordinates. Then, the ease of movement of carriers was evaluated by a Monte Carlo method. The results are shown in Table 5.

TABLE 5

| molecular orbital | 522 | 523 | 524 | 525 | 526 | 527 | 528 | 529 | 530 | 531 |
|---|---|---|---|---|---|---|---|---|---|---|
| orbital energy level (eV) | −5.441 | −5.363 | −5.334 | −5.311 | −5.307 | −5.301 | −5.28 | −5.272 | −5.243 | −5.185 |
| number of electrons | 2 | 2 | 2 | 2 | 0 | 0 | 0 | 0 | 0 | 0 |
| mobility performance index: A | 1829.8 | 56 | 675.4 | 207.4 | 150.2 | 98.8 | 395.4 | 395.2 | 853.6 | 1119.6 |
| orbital energy level (eV): B | −5.441 | −5.363 | −5.334 | −5.311 | −5.307 | −5.301 | −5.28 | −5.272 | −5.243 | −5.185 |
| standard energy level (eV): C | −5.307 | −5.307 | −5.307 | −5.307 | −5.311 | −5.311 | −5.311 | −5.311 | −5.311 | −5.311 |
| Fermi level (eV): D = (B + C)/2 | −5.374 | −5.335 | −5.321 | −5.309 | −5.309 | −5.306 | −5.296 | −5.292 | −5.277 | −5.248 |
| energy gap (eV): E = B − D | 0.067 | 0.028 | 0.013 | 0.002 | 0.002 | 0.005 | 0.016 | 0.019 | 0.034 | 0.063 |
| value of Fermi distribution function: F | 6.96E−02 | 2.53E−01 | 3.72E−01 | 4.81E−01 | 4.81E−01 | 4.52E−01 | 3.54E−01 | 3.20E−01 | 2.12E−01 | 8.03E−02 |
| maximum number of carriers of orbital: G | 2 | 2 | 2 | 2 | 2 | 2 | 2 | 2 | 2 | 2 |

TABLE 5-continued

| | | | | | | | | | |
|---|---|---|---|---|---|---|---|---|---|
| number of carriers: H = F * G | 1.39E−01 | 5.06E−01 | 7.45E−01 | 9.61E−01 | 9.61E−01 | 9.04E−01 | 7.09E−01 | 6.40E−01 | 4.23E−01 | 1.61E−01 |
| performance index of electric conductivity σ* = A * H | 254.7 | 28.3 | 502.9 | 199.4 | 144.4 | 89.3 | 280.2 | 252.8 | 361.1 | 179.8 |
| carrier | hole | | | | | electron | | | | |
| number of carriers per 1 cm³ (/cm³) | 1.86E+21 | | | | | 3.00E+21 | | | | |
| mobility (cm²/Vs) | 5.80E−04 | | | | | 7.70E−04 | | | | |

Note that if the actual measured hole mobility of NPB is unknown, instead of the actual measured value, a value obtained by using the results of non-empirical molecular orbital method calculations or density functional theory (DFT) method calculations to carry out semi-empirical molecular orbital calculations (using, for example, tight-binding quantum molecular dynamic calculation software Colors-Excite) is used. In the case of using a non-empirical molecular orbital method, the HF method, an MP2 method, an MP4 method, or the QCISD method is employed, and an initial condition of the semi-empirical quantum molecular dynamics calculation method is adjusted based on results calculated using any one of 6-31 G (d), 6-31 G (d, p), 6-311 G (d, p) and LanL2DZ as a basis function. Further, in the case of using the density functional method, an initial condition of the semi-empirical quantum molecular dynamics calculation method is adjusted based on results calculated using 6-31 G (d), 6-31 G (d, p), 6-311 G (d, p) or LanL2DZ as a basis function and B3LYP or B3PW91 as a keyword.

In addition, concerning the composite of DNTPD and molybdenum oxide, similar calculations were conducted. A value for hole mobility, $\mu$ (p)=4.13×10$^{-4}$ (cm²/Vs), was obtained, and it was estimated that the hole mobility of the composite of NPB and molybdenum oxide was larger than this value. This is consistent with experimental results in which the gradient of the voltage-current curve in the space charge limited current region shows that the composite film of NPB and molybdenum oxide has higher mobility.

The carrier mobility calculation method of the present invention is not limited to organic electroluminescent materials, and can be applied to organic materials in general, organometallic complexes, inorganic materials, organic and inorganic composite materials, semiconductors, and insulators. Moreover, the invention is not limited to films, and can also be applied to liquids. Further, the carrier mobility calculation method of the present invention can be applied to a surface or an interface of an object.

The present application is based on Japanese Patent Application serial no. 2005-376715 filed on Dec. 27, 2005 with the Japanese Patent Office, the entire contents of which are hereby incorporated by reference.

What is claimed is:

1. A method for manufacturing an electroluminescent element, comprising the steps of:
   forming the electroluminescent element comprising an anode, a cathode, and a light emitting layer comprising a material between the anode and the cathode;
   modeling a molecular model of the material;
   dividing a cell containing the molecular model into a plurality of regions;
   calculating a highest occupied molecular orbital and a lowest unoccupied molecular orbital of the molecular model;
   calculating an electron density at each of the plurality of regions in an excitation state in which one electron is excited from the highest occupied molecular orbital to the lowest unoccupied molecular orbital;
   performing a trial predetermined number of times, the trial comprising the steps of:
      determining an evaluation section comprising a first region for a starting point and a second region for an end point selected from the plurality of regions; and
      moving a carrier from the first region toward the second region in accordance with the electron density between the first region and the second region;
   counting the number of trials in which the carrier reaches the second region among all of the trials; and
   calculating a carrier mobility of the material using a probability of a carrier moving determined by the number of trials divided by the predetermined number of times.

2. A method for manufacturing an electroluminescent element, comprising the steps of:
   forming the electroluminescent element comprising an anode, a cathode, and a light emitting layer comprising a first material and a second material between the anode and the cathode;
   modeling a molecular model of the first material;
   dividing a cell containing the molecular model into a plurality of regions;
   calculating a highest occupied molecular orbital and a lowest unoccupied molecular orbital of the molecular model;
   calculating an electron density at each of the plurality of regions in an excitation state in which one electron is excited from the highest occupied molecular orbital to the lowest unoccupied molecular orbital;
   performing a trial predetermined number of times, the trial comprising the steps of:
      determining an evaluation section comprising a first region for a starting point and a second region for an end point selected from the plurality of regions; and
      moving a carrier from the first region toward the second region in accordance with the electron density between the first region and the second region;
   counting the number of trials in which the carrier reaches the second region among all of the trials; and
   calculating a carrier mobility of the first material using a probability of a carrier moving determined by the number of trials divided by the predetermined number of times.

3. The method for manufacturing the electroluminescent element according to claim 1,
   wherein the material is a hole transporting material selected from the group consisting of NPB, TPD, TDATA, MTDATA, and BSPB.

4. The method for manufacturing the electroluminescent element according to claim 2,
   wherein the first material is a hole transporting material selected from the group consisting of NPB, TPD, TDATA, MTDATA, and BSPB.

5. The method for manufacturing the electroluminescent element according to claim 1, further comprising the steps of:
   determining an initial condition of a semi-empirical quantum molecular dynamics calculation method such that the highest occupied molecular orbital, the lowest unoccupied molecular orbital, and a band gap between the highest occupied molecular orbital and the lowest unoccupied molecular orbital, which are calculated using the semi-empirical quantum molecular dynamics calculation method, fall within an error range of −0.2 to 0.2 eV inclusive, −0.2 to 0.2 eV inclusive, and −0.1 to 0.1 eV inclusive, respectively, with respect to measured values or values obtained by a first principles calculation method.

6. The method for manufacturing the electroluminescent element according to claim 5,
   wherein a non-empirical molecular orbital method or a density functional method is used as the first principles calculation method.

7. The method for manufacturing the electroluminescent element according to claim 6,
   wherein the initial condition of the semi-empirical quantum molecular dynamics calculation method is adjusted using a Hartree-Fock (HF) method, a second-order perturbation method (MP2) which takes electron correlation into account, a fourth-order perturbation method (MP4) which takes electron correlation into account, or a method in which electronic configuration interaction is found taking electron correlation and an excited state into account (a QCISD method) as the non-empirical molecular orbital method, and using any one of 6-31G (d), 6-31G (d, p), 6-311G (d, p) and LanL2DZ as a basis function.

8. The method for manufacturing the electroluminescent element according to claim 6,
   wherein the initial condition of the semi-empirical quantum molecular dynamics calculation method is adjusted using any one of 6-31G (d), 6-31G (d, p), 6-311G (d, p) and LanL2DZ as a basis function in calculations employing the density functional method.

9. The method for manufacturing the electroluminescent element according to claim 1,
   wherein the light emitting layer comprises at least one of a charge injecting layer and a charge transport layer.

10. The method for manufacturing the electroluminescent element according to claim 2, further comprising the steps of:
    determining an initial condition of a semi-empirical quantum molecular dynamics calculation method such that the highest occupied molecular orbital, the lowest unoccupied molecular orbital, and a band gap between the highest occupied molecular orbital and the lowest unoccupied molecular orbital of the first material and the second material, which are calculated using the semi-empirical quantum molecular dynamics calculation method, fall within an error range of −0.2 to 0.2 eV inclusive, −0.2 to 0.2 eV inclusive, and −0.1 to 0.1 eV inclusive, respectively, with respect to measured values or values obtained by a first principles calculation method.

11. The method for manufacturing the electroluminescent element according to claim 10,
    wherein a non-empirical molecular orbital method or a density functional method is used as the first principles calculation method.

12. The method for manufacturing the electroluminescent element according to claim 11,
    wherein the initial condition of the semi-empirical quantum molecular dynamics calculation method is adjusted using a Hartree-Fock (HF) method, a second-order perturbation method (MP2) which takes electron correlation into account, a fourth-order perturbation method (MP4) which takes electron correlation into account, or a method in which electronic configuration interaction is found taking electron correlation and an excited state into account (a QCISD method) as the non-empirical molecular orbital method, and using any one of 6-31G (d), 6-31G (d, p), 6-311G (d, p) and LanL2DZ as a basis function.

13. The method for manufacturing the electroluminescent element according to claim 11,
    wherein the initial condition of the semi-empirical quantum molecular dynamics calculation method is adjusted using any one of 6-31G (d), 6-31G (d, p), 6-311G (d, p) and LanL2DZ as a basis function in calculations employing the density functional method.

14. The method for manufacturing the electroluminescent element according to claim 1, wherein the material is an electron transporting material selected from the group consisting of $Alq_3$, $Almq_3$, $BeBq_2$, BAlq, $Zn(BOX)_2$, $Zn(BTZ)_2$, PBD, OXD-7, TAZ, p-EtTAZ, BPhen, and BCP.

15. The method for manufacturing the electroluminescent element according to claim 2, wherein one of the first material and the second material is an electron transporting material selected from the group consisting of $Alq_3$, $Almq_3$, $BeBq_2$, BAlq, $Zn(BOX)_2$, $Zn(BTZ)_2$, PBD, OXD-7, TAZ, p-EtTAZ, BPhen, and BCP.

16. The method for manufacturing the electroluminescent element according to claim 1, wherein the material is a metal oxide selected from the group consisting of zirconium oxide, hafnium oxide, vanadium oxide, niobium oxide, tantalum oxide, chromium oxide, molybdenum oxide, tungsten oxide, titanium oxide, manganese oxide, and rhenium oxide.

17. The method for manufacturing the electroluminescent element according to claim 2, wherein one of the first material and the second material is a metal oxide selected from the group consisting of zirconium oxide, hafnium oxide, vanadium oxide, niobium oxide, tantalum oxide, chromium oxide, molybdenum oxide, tungsten oxide, titanium oxide, manganese oxide, and rhenium oxide.

* * * * *

UNITED STATES PATENT AND TRADEMARK OFFICE
CERTIFICATE OF CORRECTION

| | | |
|---|---|---|
| PATENT NO. | : 8,454,748 B2 | Page 1 of 1 |
| APPLICATION NO. | : 11/643894 | |
| DATED | : June 4, 2013 | |
| INVENTOR(S) | : Iwaki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1139 days.

Signed and Sealed this
Sixth Day of January, 2015

Michelle K. Lee
*Deputy Director of the United States Patent and Trademark Office*